United States Patent
Hocquaux et al.

(10) Patent No.: US 10,947,273 B2
(45) Date of Patent: Mar. 16, 2021

(54) PEPTIDES OF USE IN THE PREVENTIVE AND CURATIVE TREATMENT OF ALOPECIA

(71) Applicants: Institut Europeen de Biologie Cellulaire, Ramonville St. Agne (FR); Centre de Recherches Biologiques et d'Experimentations Cutanees, Longjumeau (FR); Centre National de la Recherche Scientifique (CNRS), Paris (FR)

(72) Inventors: Michel Hocquaux, Paris (FR); Stéphanie Almeida Épouse Scalvino, Bourg la Reine (FR); Elian Lati, Vanves (FR); Joanna Bakala, Paris (FR)

(73) Assignees: Institut European de Biologic Cellulaire, Ramonville St. Agne (FR); Centre de Recherches Biologiques et d'Experimentations Cutanees, Longjumeau (FR); Centre National de la Recherche Scientifique (CNRS), Paris (FR)

( * ) Notice: Subject to any disclaimer, the term of this patent is extended or adjusted under 35 U.S.C. 154(b) by 73 days.

(21) Appl. No.: 15/766,860

(22) PCT Filed: Oct. 10, 2016

(86) PCT No.: PCT/EP2016/074238
§ 371 (c)(1),
(2) Date: Apr. 9, 2018

(87) PCT Pub. No.: WO2017/060533
PCT Pub. Date: Apr. 13, 2017

(65) Prior Publication Data
US 2018/0291061 A1 Oct. 11, 2018

(30) Foreign Application Priority Data
Oct. 9, 2015 (FR) ..................................... 15 59655

(51) Int. Cl.
| | | |
|---|---|---|
| *C07K 7/06* | (2006.01) | |
| *C07K 5/11* | (2006.01) | |
| *C07K 5/09* | (2006.01) | |
| *A61K 8/64* | (2006.01) | |
| *A61Q 7/00* | (2006.01) | |
| *A61K 38/00* | (2006.01) | |
| *A61K 38/06* | (2006.01) | |
| *A61K 38/07* | (2006.01) | |
| *A61K 38/08* | (2019.01) | |

(52) U.S. Cl.
CPC ............ *C07K 7/06* (2013.01); *A61K 8/64* (2013.01); *A61Q 7/00* (2013.01); *C07K 5/0817* (2013.01); *C07K 5/1019* (2013.01); *A61K 38/00* (2013.01); *A61K 38/06* (2013.01); *A61K 38/07* (2013.01); *A61K 38/08* (2013.01)

(58) Field of Classification Search
CPC .. A61Q 7/00; A61K 8/64; A61K 38/06; A61K 38/08; A61K 38/07; A61K 38/00; A61P 17/14; C07K 7/06; C07K 5/1019; C07K 5/0817
See application file for complete search history.

(56) References Cited

U.S. PATENT DOCUMENTS

2005/0080015 A1* 4/2005 Peng ...................... C07K 14/75
514/14.9

FOREIGN PATENT DOCUMENTS

| CN | 101190939 A | * | 6/2008 |
|---|---|---|---|
| CN | 102485745 A | * | 6/2012 |
| CN | 102807605 A | * | 12/2012 |
| EP | 2 894 160 | | 7/2015 |
| GB | 2 387 386 | | 10/2003 |
| WO | WO97/18239 | | 5/1997 |
| WO | WO 00/52147 | | 9/2000 |
| WO | WO 2005/009456 | | 2/2005 |
| WO | WO 2005/010027 | | 2/2005 |

OTHER PUBLICATIONS

Machine translation of CN102485745A, pp. 1-13, accessed Apr. 18, 2019.*
Machine translation of CN102807605A, pp. 1-21, accessed Apr. 18, 2019.*
Definition of Serum, from https://www.merriam-webster.com/dictionary/serum, pp. 1-2, accessed Apr. 18, 2019.*
What is Saline? from https://www.hairtransplantmentor.com/what-is-saline/, pp. 1-4, accessed Feb. 18, 2020.*
Jin et al, Ultrasound-triggered thrombolysis using urokinase-loaded nanogels, International Journal of Pharmaceutics, 2012, 434, pp. 384-390.*
Keener et al, Niacin for Stroke Prevention: Evidence and Rationale, CNS Neuroscience & Therapeutics, 2008, 14, pp. 287-294.*

(Continued)

*Primary Examiner* — Li N Komatsu

(57) ABSTRACT

The object of the present invention relates to a novel family of peptide conjugates of formula (I):

$$A\text{-}X_1\text{-}X_2\text{-}Pro\text{-}Ala\text{-}X\text{—}B \qquad (I)$$

wherein:
A represents a hydrogen atom, a $C_6$ to $C_{20}$ acyl group or a cholesterol residue;
$X_1$ represents a covalent bond, an alanine or a proline;
$X_2$ represents an arginine, a lysine, or an alanine;
X represents a lysine, an alanine, or a phenylalanine; and
B represents a hydroxyl or an amine;
or one of its preferentially pharmaceutically, dermatologically or cosmetically acceptable salts,
as well as their synthesis processes and their uses for reducing hair loss and stimulating hair growth.

14 Claims, No Drawings
Specification includes a Sequence Listing.

(56) References Cited

OTHER PUBLICATIONS

Inositol Hexanicotinate or Inositol Nicotinate BP, from http://puneetlabs.com/inositol_hexanicotinate_or_inositol_nicotinate_BP.html, 2012, pp. 1-3.*
Machine translation of CN 101190939 A, pp. 1-18, accessed Mar. 5, 2020.*
Minoxidil, from DrugBank, Aug. 21, 2014, pp. 1-9.*
Zhang et al, Substrate-Based Design of Reversible Pin1 Inhibitors, Biochemistry, 2002, 41, pp. 11868-11877.*
Ahn et al., *Effect of IGF-I on Hair Growth is Related to the Anti-Apoptotic Effect of IGF-I and Up-Regulation of PDGF-A and PDGF-B*, 24(1) Ann Dermatol. 26-31 (2012).
Bernard, *The life of the human hair follicle revealed*,22 Médecine/Sciences 138-143 (2006), Abstract only.
Danilenko et al., *Keratinocyte Growth Factor is an Important Endogenous Mediator of Hair Follicle Growth, Development and Differentiation: Normalization of the nu/nu Follicular Differentiation Defect and Amelioration of Chemotherapy-Induced Alopecia*, 147(1) American Journal of Pathology 145-154 (1995).
Donati et al., *Epidermal Wnt/β-catenin signaling regulates adipocyte differentiation via secretion of adipogenic factors*, 111 PNAS E1501-E1509 (Mar. 31, 2014).
Festa et al., *Adipocyte Lineage Cells Contribute to the Skin Stem Cell Niche to Drive Hair Cycling*, 146 Cell 761-771 (Sep. 2, 2011).
Fletcher et al., *Design of a Conformationally Defined and Proteolytically Stable Circular Mimetic of Brain-derived Neurotrophic Factor*, 283(48) Journal of Biological Chemistry 33375-33383 (Nov. 28, 2008).
Gerritsen et al., *HGF and VEGF: A Dynamic Duo*, 96 Circulation Res. 272-273 (2005).
Gille et al., *Hepatocyte Growth Factor/Scatter Factor (HGF/SF) Induces Vascular Permeability Factor (VPF/VEGF) Expression by Cultured Keratinocytes*, 11 the Journal of Investigative Dermatology 1160-1165 (1998).
Gnann et al., *Hematological and hepatic effects of vascular epidermal growth factor (VEGF) used to stimulate hair growth in an animal model*, 13(15) BMC Dermatology 1-5 (2013).
Goldman et al., *Loss of Vascular Endothelial Growth Factor in Human Alopecia Hair Follicles*, 104(5) the Journal of Investigative Dermatology 18S-20S (1995).
Guo et al., *Keratinocyte growth factor is required for hair development but not for wound healing*, 10 Genes Dev. 165-175 (1996).
Jindo et al., *Hepatocyte Growth Factor/Scatter Factor Stimulates Hair Growth of Mouse Vibrissae in Organ Culture*, 103(3) J Invest Dermatol. 306-309 (Sep. 1994).
Karlsson et al., *Roles for PDGF-A and sonic hedgehog in development of mesenchymal components of the hair follicle*, 126 Development 2611-2621 (1999).
Lachgar et al., *Minoxidil upregulates the expression of vascular endothelial growth factor in human hair dermal papilla cells*, 138 British Journal of Dermatology 407-411 (1998).
Lachgar et al., *Vascular Endothelial Growth Factor is an Autocrine Growth Factor for Hair Dermal Papilla Cells*, 106(1) the Journal of Investigative Dermatology 17-23 (Jan. 1996).
Lebdai et al., *High-grade prostate cancer and finasteride*, 105 BJIU Int. 456-459 (2009).
Lee et al., *Hepatocyte growth factor (HGF) activator expressed in hair follicles is involved in in vitro HGF-dependent hair follicle elongation*, 25 Journal of Dermatological Science 156-163 (2001).
Li et al., *Autologous Platelet-Rich Plasma: A Potential Therapeutic Tool for Promoting Hair Growth*, 38 Dermatol Surd. 1040-1046 (2012).
Li et al., *Exogenous IGF-1 promotes hair growth by stimulating cell proliferation and down regulating TGF-β1 in C57BL/6 mice* in vivo, 24 Growth Hormone & IGF Research 89-94 (2014).
Lynn R et al., *Therapeutic Hotline. Treatment of androgenic alopecia with finasteride may result in a high grade prostate cancer in patients: fact or fiction?*, 23 Dermatological Therapy 544-546 (2010).
Mecklenburg et al., *Active Hair Growth (Anagen) is Associated with Angiogenesis*, 114(5) the Journal of Investigative Dermatology. 909-916 (2000).
Randall et al., *Stem cell factor/c-Kit signaling in normal and androgenetic alopecia hair follicles*, 197 Journal of Endocrinology 11-23 (2008).
Reimer et al., *Side-chain Effects on Peptidyl-prolyl cis/trans Isomerisation*, 279 J. Mol. Biol 449-460 (1998).
Rogers, *Commentary on Autologous Platelet-Rich Plasma: A Potential Therapeutic Tool for Promoting Hair Growth*, 38 Dermatological Surgery 1047-1048 (2012).
Shimaoka et al., *Hepatocyte Growth Factor/Scatter Factor Expressed in Follicular Papilla Cells Stimulates Human Hair Growth in Vitro*, 165 Journal of Cellular Physiology 333-338 (1995).
Shimaoka et al., *Dermal papilla cells express hepatocyte growth factor*, 7(Suppl) Journal of Dermatological Science S79-S83 (1994).
Su et al., *Insulin-like growth factor 1 and hair growth*, 5(1) Dermatology Online Journal 1-17 (1999).
Tomita et al., *PDGF isoforms induce and maintain anagen phase of murine hair follicles*, 43 J Dermatol Sci. 105-115 (2006).
Yano et al., *Control of hair growth and follicle size by VEGF-mediated angiogenesis*, 107(4) J Clin Invest. 409-417 (2001) (abstract only).
van der Steen et al., *The Genetic Risk for Alopecia Areata in First Degree Relatives of Severely Affected Patients*, 72 Acta Derm Venereol. 373-375 (1992).
Zhou et al., *Dynamic changes in nerve growth factor and substance P in the murine hair cycle induced by depilation*, 33 Journal of Dermatology 833-841 (2006).
International Search Report dated Feb. 16, 2017, in corresponding PCT Application PCT/EP2016/074238.
Preliminary Search Report dated May 26, 2016, in corresponding French Patent Application No. 1559655.

* cited by examiner

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial
<220> FEATURE:
<223> OTHER INFORMATION: Synthetic peptide

<400> SEQUENCE: 1

Ala Arg Pro Ala Lys
1               5

<210> SEQ ID NO 2
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palm-Ala
```

```
<400> SEQUENCE: 2

Ala Arg Pro Ala Lys
1               5

<210> SEQ ID NO 3
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palm-Ala
<220> FEATURE:
<221> NAME/KEY: MOD_RES
<222> LOCATION: (5)..(5)
<223> OTHER INFORMATION: AMIDATION

<400> SEQUENCE: 3

Ala Arg Pro Ala Lys
1               5

<210> SEQ ID NO 4
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palm-Ala
<220> FEATURE:
<221> NAME/KEY: MOD_RES
<222> LOCATION: (5)..(5)
<223> OTHER INFORMATION: AMIDATION

<400> SEQUENCE: 4

Ala Arg Pro Ala Ala
1               5

<210> SEQ ID NO 5
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palm-Ala
<220> FEATURE:
<221> NAME/KEY: MOD_RES
<222> LOCATION: (5)..(5)
<223> OTHER INFORMATION: AMIDATION

<400> SEQUENCE: 5

Ala Arg Ala Ala Lys
1               5

<210> SEQ ID NO 6
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
```

```
<223> OTHER INFORMATION: Palm-Ala
<220> FEATURE:
<221> NAME/KEY: MOD_RES
<222> LOCATION: (5)..(5)
<223> OTHER INFORMATION: AMIDATION

<400> SEQUENCE: 6

Ala Ala Pro Ala Lys
1               5

<210> SEQ ID NO 7
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Chol-Ala
<220> FEATURE:
<221> NAME/KEY: MOD_RES
<222> LOCATION: (5)..(5)
<223> OTHER INFORMATION: AMIDATION

<400> SEQUENCE: 7

Ala Arg Pro Ala Lys
1               5

<210> SEQ ID NO 8
<211> LENGTH: 4
<212> TYPE: PRT
<213> ORGANISM: Artificial
<220> FEATURE:
<223> OTHER INFORMATION: Synthetic peptide

<400> SEQUENCE: 8

Arg Pro Ala Lys
1

<210> SEQ ID NO 9
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Palm-Arg

<400> SEQUENCE: 9

Arg Pro Ala Lys
1

<210> SEQ ID NO 10
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: H-Ala or C6 to C20-Ala or Chol-Ala acyl group
<220> FEATURE:
<221> NAME/KEY: VARIANT
<222> LOCATION: (1)..(1)
<223> OTHER INFORMATION: Ala can be replaced by Pro
<220> FEATURE:
<221> NAME/KEY: VARIANT
```

```
<222> LOCATION: (2)..(2)
<223> OTHER INFORMATION: Arg can be replaced by Lys or Ala
<220> FEATURE:
<221> NAME/KEY: VARIANT
<222> LOCATION: (5)..(5)
<223> OTHER INFORMATION: Lys can be replaced by Ala or Phe
<220> FEATURE:
<221> NAME/KEY: BINDING
<222> LOCATION: (5)..(5)
<223> OTHER INFORMATION: Lys-OH or Lys-NH2

<400> SEQUENCE: 10

Ala Arg Pro Ala Lys
1               5

<210> SEQ ID NO 11
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: H-Arg or C6 to C20-Arg or Chol-Arg acyl group
<220> FEATURE:
<221> NAME/KEY: VARIANT
<222> LOCATION: (1)..(1)
<223> OTHER INFORMATION: Arg can be replaced by Lys or Ala
<220> FEATURE:
<221> NAME/KEY: VARIANT
<222> LOCATION: (4)..(4)
<223> OTHER INFORMATION: Lys can be replaced by Ala or Phe
<220> FEATURE:
<221> NAME/KEY: BINDING
<222> LOCATION: (4)..(4)
<223> OTHER INFORMATION: Lys-OH or Lys-NH2

<400> SEQUENCE: 11

Arg Pro Ala Lys
1
```

PEPTIDES OF USE IN THE PREVENTIVE AND CURATIVE TREATMENT OF ALOPECIA

CROSS-REFERENCE TO RELATED APPLICATIONS

This application is a U.S. National Stage Application pursuant to 35 U.S.C. § 371 of International Patent Application PCT/EP2016/074238, filed on Oct. 10, 2016, and published as WO 2017/060533 on Apr. 13, 2017, which claims priority to French Patent Application 1559655, filed on Oct. 9, 2015, all of which are incorporated herein by reference in their entireties for all purposes.

The object of the present invention relates to a novel family of peptide compounds as well as their synthesis processes and their use for reducing hair loss and stimulating hair growth.

Introduction

Appearance is an important social factor in our times. One's head of hair has a strong symbolic value; it is a large part of one's self-image and of the image one presents to others. Hair loss is a real problem which many people experience as a handicap. For that reason, the head of hair is the main focus of the hair-care sector, which accounts for a quarter of the global cosmetics market. Consequently, there is an ongoing search for effective, side-effect-free active agents for stopping or reducing hair loss (alopecia).

Today, in France, more than 10 million people are concerned by abnormal hair loss. It affects practically 2 men out of 3 and 1 woman out of 5 (generally after menopause). The causes of abnormal loss of hair can be diverse: ageing hair, diseases such as cancer or lupus, hormonal changes, stress, certain medications, or nutritional deficiencies.

The human head of hair represents a collection of about 100,000 individual hairs. All these hairs are created, live and then die to then be replaced by new growth. Each one is produced by the hair follicle, which is an autonomous skin appendage with its own hormonal control, its own cycle, and a complex and stable structure (Bernard B A, "*The life of the human hair follicle revealed.*" *Médecine/Sciences* 2006; 22:138-43 [in French]). The follicles serve as a "reservoir" of stem cells capable of giving rise to all the cell lines needed to reconstitute the follicles themselves, the epidermis, and the sebaceous glands.

Hair, the lifespan of which varies from 2 to 7 years, does not grow continuously but according to a cycle which can vary by individual, the individual's age, and the seasons. The hair cycle is composed of three phases: the anagen or growth phase (which lasts from three to five years), the catagen phase (which lasts one or two weeks) which is the rest period, and the telogen phase where the hair dies. Following this last phase, which leads to hair loss, the follicle regenerates by a process of neomorphogenesis from a reservoir of stem cells and initiates a new anagen phase.

In a normal head of hair being constantly renewed, about 85% of the follicles are in growth phase, 2% in rest phase and more than 10% in loss phase. During a lifetime, 20 or so cycles occur, never all in the same phase (asynchronous), which enables us to keep a satisfactory head of hair. Repeated damage, a poor diet, disease, stress, and pollution can however threaten the hair cycle.

Under physiological conditions, each day we lose between 50 and 100 hairs having reached the telogen phase. Beyond that number, the loss is considered excessive and should be treated. Alopecia is a term for designating hair loss over all or part of the scalp which leaves the skin partially or completely bare. It affects about 20% of men starting at 20 years of age, then it increases about 10% every 10 years. Beyond 50 years of age, therefore, a little more than half of men have a certain degree of baldness. If abnormal hair loss is generally the privilege of men, this condition can also affect certain women and become a true aesthetic handicap.

Congenital, acquired, localized, diffuse, acute or chronic, various forms of alopecia exist, the causes and mechanisms of which are diverse. Depending on the origin of the baldness, the hair can regrow more or less easily. No all-purpose treatment exists; each case of alopecia is complex and must be the object of suitable treatment.

Androgenetic alopecia is the most common form of hair loss and the leading cause of baldness in both men and women. It results in a progressive and permanent reduction in hair quality and quantity. Androgenetic alopecia results from the hair follicles being oversensitive to dihydrotestosterone (DHT), a male hormone, produced from testosterone. DHT shortens the hair-growth (anagen) phase, and consequently more quickly reduces the number of potential hair follicle cycles. The hair thus ends up disappearing, the so-called "miniaturization" of the hair.

Oral administration of oral antiandrogens such as finasteride (Propecia®), which blocks 5-alpha reductase, an enzyme responsible for the transformation of testosterone into DHT at the hair follicles, reduces hair loss and activates hair regrowth. However, this product, which inspired great hope, is contraindicated in women and recent warnings have been announced as regards its use in men. Indeed, the results of a clinical study suggest that patients taking this medicine risk developing a serious form of prostate cancer (Lynn R et al., "*Therapeutic hotline. Treatment of androgenic alopecia with finasteride may result in a high grade prostate cancer in patients: fact or fiction?*" *Dermatol Ther.* 2010; 23:544. Lebdai S et al., *High-grade prostate cancer and finasteride. BJU Int.* 2010; 105:456).

In addition, minoxidil (Rogaine®) and Aminexil®, two topical solutions applied to the scalp, also prove effective in the treatment of alopecia. Their anti-hair-loss properties are associated with stimulation of blood microcirculation which ensures the good health of our hair (Mecklenburg L et al., "*Active hair growth (anagen) is associated with angiogenesis.*" *J Invest Dermatol.* 2000; 114:909. Lachgar S et al., "*Minoxidil upregulates the expression of vascular endothelial growth factor in human hair dermal papilla cells.*" *Br J Dermatol.* 1998; 138:407).

However, those two products are useful only at the onset of alopecia and their efficacy remains limited because hair loss resumes when the treatment is discontinued. Moreover, daily use is likely the origin of the undesirable side effects observed in patients using them over a long period such as local skin reactions or systemic effects. In addition, the percentage of responders is below 50%.

The current hair-care market proposes numerous treatments for strengthening the hair fibre and slowing excessive hair loss. However, generally speaking, they are insufficiently effective, notably because they very often attack only one of the causes directly involved in the alopecia phenomenon. There also exist purely cosmetic products containing agents specifically for giving volume to a thin head of hair. These agents do not stimulate growth, however. They can, nevertheless, give the impression of a thicker head of hair by coating the hair shaft, thus increasing its diameter. These products offer only a temporary solution since they disappear after each shampooing.

Therefore, researchers have their sights set on targeted research having the objective of identifying novel compounds for stopping or reducing alopecia. One often-explored avenue is the investigation of novel molecules capable of influencing expression of the growth factors which manage hair growth.

Indeed, hair follicle homeostasis and hair growth remain under the control of numerous growth factors. That is why a procedure performed in the physician's office, consisting in injecting autologous platelet extracts into the scalp, enables an improvement in the state of the head of hair (Li et al., "*Autologous platelet-rich plasma: a potential therapeutic tool for promoting hair growth.*" Dermatol Surg. 2012; 38:1040). Platelet extracts, by their wealth of growth factors (VEGF, PDGF, bFGF and HGF), regenerate hair, slow hair loss and promote hair regrowth.

First among the factors taking part in regulation of the hair cycle is platelet-derived growth factor (PDGF). PDGF is a cytokine which plays a central role in hair growth and in activation of the follicular stem cell (Karlsson et al., "*Roles for PDGF-A and sonic hedgehog in development of mesenchymal components of the hair follicle.*" Development. 1999; 126:2611. Tomita et al., "*PDGF isoforms induce and maintain anagen phase of murine hair follicles.*" J Dermatol Sci. 2006; 43:105).

Indeed, PDGF-induced proliferation of follicular cells is 100 times faster than that observed for other cell targets of this factor. It has been shown that PDGF production by adipocyte precursors present at the base of the hair follicle is essential under physiological conditions for initiating the anagen phase (Festa et al., "*Adipocyte lineage cells contribute to the skin stem cell niche to drive hair cycling.*" Cell. 2011; 146:761). Indeed, when hair dies, the fat layer in the scalp shrinks. The development of PDGF-producing adipose tissue has proved necessary to hair regeneration.

A recent study showed the role of the epidermis in secretion of the factors responsible for adipogenesis: IGF1, BMP2 and BMP6. These factors, by stimulating lipocyte growth, induce production of PDGF which, in turn, acts on the follicle to activate hair growth (Donati et al., "*Epidermal Wnt/ β-catenin signaling regulates adipocyte differentiation via secretion of adipogenic factors.*" Proc Natl Acad Sci U.S.A. 2014; 111:E1501). There is thus a global physiological synchronization between the adipose tissue and the follicle, with an initiating signal coming from the epidermis.

This discovery of the source of signals that trigger hair growth can lead to the development of novel active agents for treating baldness. Moreover, compounds having a stimulatory effect on PDGF production are potential candidates for deeper research in the alopecia field.

The role of vascular endothelial growth factor (VEGF) in scalp homeostasis is also extensively described. Indeed, it is well-known that good blood flow to the scalp is essential for preserving the hair and that the length of the hair anagen phase depends on the presence of VEGF.

It has been shown that VEGF, a powerful proangiogenic factor, stimulates vasculature formation at the hair follicle and feeds the root throughout the anagen phase. This is the determining factor for a successful hair cycle (Yano et al., "*Control of hair growth and follicle size by VEGF-mediated angiogenesis.*" J Clin Invest. 2001; 107:409). The demonstration of local VEGF production by dermal papilla cells corroborates the contribution of this cytokine to hair growth (Lachgar et al., "*Vascular endothelial growth factor is an autocrine growth factor for hair dermal papilla cells.*" J Invest Dermatol. 1996; 106:17-23). A significant reduction in VEGF level in people suffering hair loss confirms the importance of this cytokine in preserving our potential for hair (Goldman et al., "*Loss of vascular endothelial growth factor in human alopecia hair follicles.*" J. Invest Dermatol. 1995; 104:18).

That is why stimulation of VEGF production at the follicle is one of the promising ways for stimulating hair growth and ensuring good hair health (Gnann et al., "*Hematological and hepatic effects of vascular epidermal growth factor (VEGF) used to stimulate hair growth in an animal model.*" BMC Dermatology 2013; 13:15).

Hepatocyte growth factor (HGF) is a multifunctional cytokine also involved in control of follicle activity. The stimulatory effect of HGF on hair growth has been widely shown (Jindo et al., "*Hepatocyte growth factor scatter factor stimulates hair growth of mouse vibrissae in organ culture.*" J Invest Dermatol. 1994; 103(3):306. Shimaoka et al., "Hepatocyte growth factor/scatter factor expressed in follicular papilla cells stimulates human hair growth in vitro." J Cell Physiol. 1995; 165:333. Lee et al., "*Hepatocyte growth factor (HGF) activator expressed in hair follicles is involved in in vitro HGF-dependent hair follicle elongation.*" J Dermatol Sci. 2001; 25:156). Moreover, HGF induces VEGF expression by keratinocytes and in this way contributes to the angiogenesis process (Gille et al., "*Hepatocyte Growth Factor/Scatter Factor (HGF/SF) Induces Vascular Permeability Factor (VPF/VEGF) Expression by Cultured Keratinocytes.*" J Invest Dermatol. 1998; 11:1160. Gerritsen et al., HGF and VEGF: a dynamic duo. Circulation Res. 2005; 96:272).

In addition, in the same way as for VEGF, HGF is produced locally by dermal papilla cells (Shimaoka et al., "*Dermal papilla cells express hepatocyte growth factor.*" J Dermatol Sci. 1994; 7 Suppl:S79).

Keratinocyte growth factor (KGF/FGF7) also belongs to the family of cytokines involved in normal hair growth. KGF acts directly in the production of keratinocytes by the matrix and strengthens keratin cohesion by thus stimulating hair growth, most of which is made up of keratinocytes. (Danilenko et al., "*Keratinocyte growth factor is an important endogenous mediator of hair follicle growth, development and differentiation: normalization of the nu/nu follicular differentiation defect and amelioration of chemotherapy-induced alopecia.*" Am J Pathol. 1995; 147 (1):145. Guo et al., "*Keratinocyte growth factor is required for hair development but not for wound healing.*" Genes Dev. 1996; 10:165).

A multitude of other growth factors is also involved in control of the hair cycle. Among these, mention must be made of, among others, stem cell factor (SCF or kit-ligand) (Randall et al., "*Stem cell factor/c-Kit signalling in normal and androgenetic alopecia hair follicles.*" J Endocrinol. 2008; 197:11), nerve growth factor (NGF) (Zhou et al., "*Dynamic changes in nerve growth factor and substance P in the murine hair cycle induced by depilation.*" Dermatol. 2006; 33:833), as well as insulin-like growth factor 1 (IGF1) (Ahn et al., Effect of IGF-1 on hair growth is related to the anti-apoptotic effect of IGF-1 and up-regulation of PDGF-A and PDGF-B. Ann Dermatol. 2012; 24:26. Su et al., Insulin-like growth factor 1 and hair growth. Dermatol Online J. 1999; 5:1. Li et al., "*Exogenous IGF-1 promotes hair growth by stimulating cell proliferation and down regulating TGF-β1 in C57BL/6 mice in vivo.*" Growth Horm IGF Res. 2014; 24:89).

It should be noted that an increase in synthesis at least of one of the above-mentioned factors following treatment with an active agent should result in an improvement in hair growth.

Alopecia is described as a "polygenic" phenomenon because the modulation of several genes is involved in hair loss. In addition, genetic predispositions are recognized as one of the factors influencing the appearance of baldness (van der Steen P, Traupe H, Happle R, Boezeman J, Strater R, Hamm H. "*The genetic risk for alopecia areata in first degree relatives of severely affected patients. An estimate.*" Acta Derm Venereol. 1992; 72:373). Indeed, a third of men suffer from baldness before 45 years of age, a hereditary phenomenon dependant on a conjunction of genetic factors.

This invention describes a stimulatory effect of a novel family of peptides on growth of hair kept alive ex vivo. These data associated with the inductive effects of these peptides on the proliferation of cells forming part of the human hair follicle and on the production of the growth factors involved in the hair cycle lead us to propose a preparation, containing at least one of these peptides, which would make it possible to stop or reduce alopecia, and especially to induce or stimulate hair growth and/or to increase hair density and/or to reduce hair loss.

SUMMARY OF THE INVENTION

The object of the present invention thus relates to a peptide conjugate of formula (I):

A-X$_1$—X$_2$-Pro-Ala-X—B    (I)

wherein:
A represents a hydrogen atom, a C$_6$ to C$_{20}$ acyl group or a cholesterol residue;
X$_1$ represents a covalent bond, an alanine or a proline;
X$_2$ represents an arginine, a lysine, or an alanine;
X represents a lysine, an alanine, or a phenylalanine; and
B represents a hydroxyl or an amine;
or one of its preferentially pharmaceutically, dermatologically or cosmetically acceptable salts.

The object of the present invention further relates to a process for manufacturing the peptide conjugate of formula (I) above, characterized in that said process comprises the following successive steps:
a. synthesis, at least partially on solid support, of the peptide strand of formula H—X$_1$—X$_2$-Pro-Ala-X—B, wherein
X$_1$, X$_2$, X are as defined above and (the reactive groups of which) are suitably protected;
B is the solid support or a suitably protected OH or NH$_2$ group;
b. optional grafting of group A onto the peptide strand of step (a) by acylation reaction (when it is desired that A is not a hydrogen atom), preferentially by the use of an activated acyl in the presence of a base;
c. deprotection of the protected amino acids optionally together with cleavage of the peptide from the resin, when B is a solid support;
d. optional purification of the peptide conjugate of formula (I) obtained, for example by HPLC; and
e. collection of the product of formula (I).

Moreover, the object of the present invention relates to a cosmetic use of a peptide conjugate of formula (I) as defined herein for reducing hair loss and/or stimulating hair growth.

Another object of the present invention relates to a pharmaceutical, cosmetic or dermatological treatment method for combating alopecia, and/or for stimulating hair growth, comprising the administration to a patient of a peptide conjugate of formula (I) as defined herein.

More particularly, the object of the present invention relates to a treatment method as above, characterized in that the administration is carried out by applying to the scalp a composition comprising at least one peptide described above. Advantageously, the object of the present invention relates to a treatment method as above, characterized in that at least one peptide described above is combined with another dermatological active ingredient, for example which improves activity on hair regrowth and has been described for that activity.

Among these compounds, mention may be made of:
minoxidil,
nicotinic acid esters,
5α-reductase inhibitors, or
another peptide with dermatological activity.

In particular, exemplary peptides with dermatological activities which can be combined with the peptides according to the present invention include those found in application PCT WO97/18239 or WO2005/009456 for these particular embodiments.

The object of the present invention also relates to a peptide conjugate of formula (I) as defined herein, as medicinal product.

The object of the present invention thus relates to a peptide conjugate of formula (I) as defined herein, for dermatological use optionally in combination with another preferentially dermatological active ingredient, such as those which improve activity on regrowth and have been described for that activity, more particularly those cited above (minoxidil, nicotinic acid esters, 5α-reductase inhibitors and other peptides with dermatological activity such as those found in application PCT WO97/18239 or WO2005/009456).

Equally advantageously, the present invention relates to a peptide conjugate of formula (I) as defined herein, for dermatological use, as sole active ingredient.

The present invention further relates to a peptide conjugate of formula (I) as defined herein, for use in the treatment or the prevention of alopecia.

In a complementary manner, the object of the present invention thus relates to a pharmaceutical, dermatological or cosmetic composition comprising at least one peptide conjugate of formula (I) as defined herein.

Definitions

"Peptide Conjugate"/"Peptide Strand"

The term "peptide" (equivalent to the term "oligopeptide") should be understood to mean polymers of amino acids, said amino acids being linked together by a peptide bond. A peptide bond is an amide bond linking two amino acids. A peptide generally contains between 2 and 80 to 100 amino acids, the upper limit not being clearly defined, but general relates to the domain of proteins. Thus, a "dipeptide" is a polymer fragment of two amino acids linked together by a peptide bond. A tripeptide is a polymer fragment of three amino acids linked together by a peptide bond, etc.

Within the context of the present application, the peptides or peptide conjugates are tetrapeptides (i.e., composed of 4 amino acids) or pentapeptides (composed of 5 amino acids).

When the expression "peptide conjugate", "peptide strand" or "peptide fragment" is used, these expressions simply refer to the succession of the amino acids concerned.

Conventionally, peptides (or proteins) can be extracted from a biological medium or manufactured synthetically. Preferably, the peptides according to the present invention are synthesized. Peptide synthesis techniques are described in Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodman Ed., Georg Thieme Verlag, 2002. Peptide synthesis can be carried out in liquid medium or on solid support. Both techniques are applicable to the present invention. Nevertheless, for practical considerations, synthesis on solid support is preferred according to the present invention.

The names typically used in the peptide synthesis field are applicable herein. For example, the terms "Ala" or "A" correspond to alanine, "Pro" or "P" to proline, "Arg" or "R" to arginine, "Lys" or "K" to lysine, "Phe" or "F" to phenylalanine, etc.

The amino acids involved in the peptide conjugate of formula (I) according to the present invention can be in L or D configuration, according to the stereochemistry of their asymmetrical carbon. The "L" form exclusively is preferred, as natural amino acids are in that form. Moreover, mixtures of L and D forms of the same amino acid can be used for the synthesis of a peptide conjugate of formula (I) according to the present invention. The 50/50% (±10%) by mass racemic mixture is designated "L/D". In the case of amino acid mixtures, the L/D mixture is preferred, as it is easily obtained. Nevertheless, the object of the present invention also relates to a peptide of formula (I) above obtained by the use of any type of mixture of "L" or "D" form of amino acid concerned.

Furthermore, according to the present invention, the term "amino acid side chain" represents the fragment attached to the α carbon of an amino acid. For example, the side chains of natural amino acids such as glycine, valine, alanine and aspartic acid correspond to the hydrogen atom and isopropyl, methyl and $CH_2COOH$ groups, respectively.

Amino acid side chains can be protected by protecting groups (P) and more particularly N-protecting or O-protecting groups when said chains contain the corresponding heteroatoms.

Protecting groups (P) are groups known to the person skilled in the art. Said protecting groups and their use are described in works such as, for example, "Greenes Protective Groups in Organic Synthesis", Wiley, New York, 2007 4th edition; Harrison et al. "Compendium of Synthetic Organic Methods", Vol. 1 to 8 (J. Wiley & Sons, 1971 to 1996); Paul Lloyd-Williams, Fernando Albericio, Ernest Giralt, "Chemical Approaches to the Synthesis of Peptides and Proteins", CRC Press, 1997 or Houben-Weyl, "Methods of Organic Chemistry, Synthesis of Peptides and Peptidomimetics", Vol E 22a, Vol E 22b, Vol E 22c, Vol E 22d., M. Goodman Ed., Georg Thieme Verlag, 2002. When these protecting groups are attached to a nitrogen atom, they are called N-protecting groups. The same applies to O-protecting groups, etc. For example, a hydroxy can be protected by a trityl group, or a carboxylic acid can be protected in the form of a tert-butyl ester. When synthesis is carried out on solid support, it is the resin which serves as protecting group for the C-terminal carboxylic function.

Protection of the amino group of the amino acid can be carried out for example by a tert-butyloxycarbonyl group (hereinafter referred to as Boc-) or a 9-fluorenylmethyloxycarbonyl group (hereinafter referred to as Fmoc) represented by the formula:

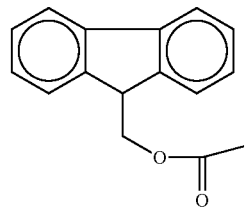

In particular, the so-called "Fmoc/tBu" strategy is preferred due to its ease of implementation. The term "tBu" is understood to mean that the side chains are protected by acid-labile groups such as tBu used most commonly in this strategy. Other protecting groups of functions attached to the side chains can thus be the "Boc" group (for lysine, for example) or the "Pbf" group (for arginine, for example). Thus, protection is carried out according to the known processes of the prior art. For example, protection by the Boc- group can be obtained by reacting the amino acid with di-tert-butylpyrocarbonate ($Boc_2O$).

As indicated above, A can be a hydrogen, a $C_6$ to $C_{20}$ acyl group or a cholesterol residue.

When A is an acyl group, it is a linear $C_6$ to $C_{20}$ acyl group, particularly a linear $C_{10}$ to $C_{16}$ acyl group, and more particularly a linear $C_{16}$ acyl group, i.e., a palmitoyl group.

Within the context of the present invention, the term acyl corresponds to a radical or a functional group obtained by removing the hydroxyl group from a carboxylic acid. The acyl group corresponding to a carboxylic acid of formula RCOOH can have the formula RCO—, where the carbon atom and the oxygen atom are linked by a double bond (carbonyl group). A $C_6$ to $C_{20}$ acyl group thus corresponds to a linear or branched, preferentially linear, saturated hydrocarbon chain comprising from 6 to 20 carbon atoms including a "—C=O—" group linking this hydrocarbon chain to the molecule to which it is attached.

A can also be a cholesterol residue.

Cholesterol is a lipid of the sterol family which is involved in many biochemical processes.

The formula of cholesterol is:

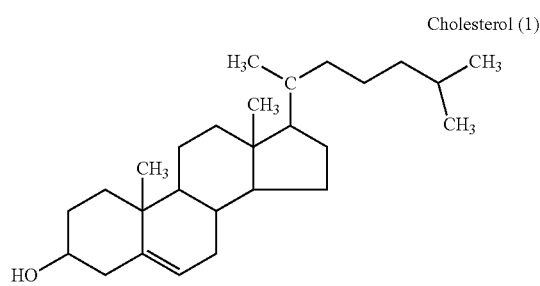 [SMILES: CC(C)CCCC(C)C1CCC2C3CC=C4CC(O)CCC4(C)C3CCC12C]

Cholesterol (1)

Nevertheless, several chiral centres are present in this molecule, and preferably, the cholesterol used for the present invention is:

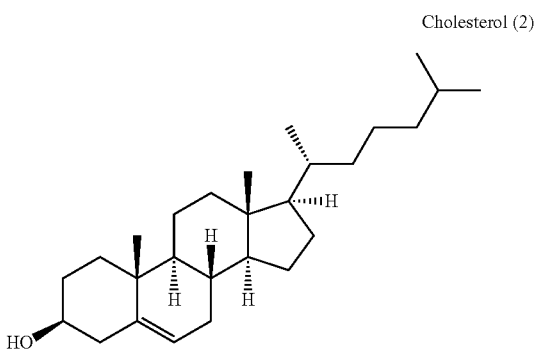

Cholesterol (2)

Thus, according to the present invention, the term "cholesterol residue" is understood to mean that the OH group of the cholesterol molecule is engaged in an ester bond with group $X_1$.

The term "hydroxyl" according to the present invention relates to the —OH fragment, and optionally its salts, for example sodium or potassium.

DETAILED DESCRIPTION

The object of the present invention thus relates to a peptide conjugate of formula (I) as defined herein, characterized in that group A represents a hydrogen atom, a $C_{10}$ to $C_{20}$ acyl group, preferentially a palmitoyl C16 acyl group or a cholesterol residue according to formula (II):

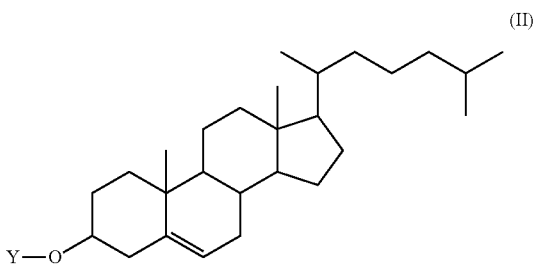

(II)

wherein:
Y represents the carbon atom of the ester bond between the cholesterol residue and $X_1$.

Furthermore, the object of the present invention relates to a peptide conjugate of formula (I) as defined herein, characterized in that group A represents a hydrogen atom, a palmitoyl group or a cholesterol residue.

When A is a cholesterol residue, it is understood that group Y of formula (II) above represents the carbon atom of the ester bond formed between the cholesterol and $X_1$.

The object of the present invention further relates to a peptide conjugate of formula (I) as defined herein, characterized in that the salt is an acid addition salt, wherein the acid is for example hydrochloric acid, trifluoroacetic acid and/or acetic acid. Preferably, the acid is selected so as to increase the lipophilicity of the peptide conjugate of formula (I) and thus to help it penetrate the skin.

The object of the present invention further relates to a peptide conjugate of formula (I) as defined herein, characterized in that $X_1$ is an alanine or a covalent bond, and $X_2$ is an arginine or an alanine.

The object of the present invention advantageously relates to a peptide conjugate of formula (I) as defined herein, characterized in that it is selected from:
(1) H-Ala-Arg-Pro-Ala-Lys-OH (see SEQ ID NO:1),
(2) Palm-Ala-Arg-Pro-Ala-Lys-OH (see SEQ ID NO:2),
(3) Palm-Ala-Arg-Pro-Ala-Lys-$NH_2$ (see SEQ ID NO:3),
(4) Palm-Ala-Arg-Pro-Ala-Ala-$NH_2$ (see SEQ ID NO:4),
(5) Palm-Ala-Arg-Ala-Ala-Lys-$NH_2$ (see SEQ ID NO:5),
(6) Palm-Ala-Ala-Pro-Ala-Lys-$NH_2$ (see SEQ ID NO:6),
(7) Chol-Ala-Arg-Pro-Ala-Lys-$NH_2$ (see SEQ ID NO:7),
(8) H-Arg-Pro-Ala-Lys-OH (see SEQ ID NO:8), or
(9) Palm-Arg-Pro-Ala-Lys-OH (see SEQ ID NO:9),
wherein
Palm represents a palmitoyl group and
Chol represents the cholesterol residue.

Preferably, the object of the present invention relates to a peptide conjugate of formula (I) for use in the treatment or the prevention of alopecia, characterized in that the alopecia is selected from androgenetic, congenital, acquired, localized, diffuse, acute or chronic alopecia.

The object of the present invention further relates to a pharmaceutical, dermatological or cosmetic composition comprising at least one peptide conjugate of formula (I) as defined herein further characterized in that it is a composition for topical use.

The object of the present invention also relates to a composition as defined above characterized in that said composition comprises a peptide conjugate of formula (I) in the form of enantiomers and/or of diastereoisomers, preferentially the amino acids of the peptide conjugate being of L or D form exclusively (i.e., higher than a 95/5% ratio) or of L/D form (i.e., 50/50%±10%).

The object of the present invention further relates to a composition as defined above characterized in that it is a composition for the scalp.

The object of the present invention thus relates to a composition as defined above characterized in that said composition is selected from a lotion, a serum, a shampoo, such as a medicated shampoo, a spray, a gel or a cream such as a medicated cream.

The object of the present invention relates to a composition as defined above characterized in that said composition comprises at least one peptide of formula (I) as described above at a concentration ranging between $10^{-9}$ and $10^{-4}$ mole/litre of composition, preferably between $10^{-7}$ and $10^{-5}$ mole/litre of composition.

The object of the present invention thus relates to the cosmetic use of a composition as defined above for reducing hair loss and/or stimulating hair growth.

The object of the present invention also relates to a composition as defined above, as medicinal product.

The object of the present invention preferentially relates to a composition as defined above for dermatological use optionally comprising in combination with the peptide conjugate of formula (I) according to the invention, another preferentially dermatological active ingredient such as those defined above.

The object of the present invention further relates to a composition as defined above for use in the treatment or the prevention of alopecia.

The object of the present invention relates to a composition as defined above for its use above, characterized in that the alopecia is selected from androgenetic, congenital, acquired, localized, diffuse, acute or chronic alopecia.

EXAMPLES

The following examples illustrate the present invention but in no way limit its scope.
I. Synthesis
Solid phase peptide synthesis, according to the following examples, was carried out according to a Fmoc/tBu strategy.

A known amount of resin is introduced into a reactor then coupling and deprotection cycles are repeated until the desired peptide is obtained.

The peptide is then cleaved from the resin then isolated by precipitation then purified.

The peptides were synthesized on Rink-amide resin. The couplings were carried out with HBTU as coupling agent and DIEA as base.

At the end of the synthesis, side chain cleavage and deprotection were carried out according to the following protocol for Rink-amide resin.

A. Cleavage From the Resin:

Cleavage from the Rink-amide resin is accomplished with TFA in a proportion of about 10 mL/g resin for 1 h.

After 1 hour, the resin is filtered then rinsed with DCM. The filtrate is then concentrated under vacuum and the peptide is isolated by precipitation in ether then centrifuged.

The supernatant is then removed, then the pellet is dried under vacuum.

The final compounds were characterized by analytical HPLC and LC/MS mass spectrometry.

Yields were calculated based on the initial loading of the resin.

B. Acylation of the Peptides:

P1: Palmitoylation of the Peptides

Place DCM in the reactor containing the supported peptide (the peptide must be deprotected on the N-terminal side) and allow the resin to swell for 15 min.

Dissolve 3 equivalents of Palm-Cl (equivalents based on resin loading) in DCM. Next empty the reactor and add Palm-Cl dissolved in DCM then stir for 3 h.

Wash the resin and dry under vacuum.

P2: Grafting of Cholesterol onto the Peptides

Place DCM in the reactor containing the supported peptide (the peptide must be deprotected on the N-terminal side) and allow the resin to swell for 15 min. Solubilize 3 equivalents of cholesterol (equivalents based on resin loading) in the form of cholesterol chloroformiate in DCM.

Add Cholesteryl-Cl (a synonym for cholesterol chloroformiate) dissolved in DCM then stir for 3 h.

Wash the resin and dry under vacuum.

Synthesis of peptide (3) Palm-Ala-Arg-Pro-Ala-Lys-NH$_2$ (see SEQ ID NO:3)

The peptide was palmitoylated according to protocol P1 then the peptide was cleaved from the resin and was purified by preparative HPLC. Yield: 40%; Purity: 93%; LCMS: m/z 779.7 [M+H]$^+$ Synthesis of peptide (7) Chol-Ala-Arg-Pro-Ala-Lys-NH$_2$ (see SEQ ID NO:7)

The cholesterol was grafted according to protocol P2 then the peptide was cleaved from the resin and was purified by preparative HPLC. Yield: 50%; Purity: 97%; LCMS: m/z 953.8 [M+H]$^+$ Synthesis of peptide (5) Palm-Ala-Arg-Ala-Ala-Lys-NH$_2$ (see SEQ ID NO:5)

The peptide was palmitoylated according to protocol P1 then the peptide was cleaved from the resin and was purified by preparative HPLC. Yield: 60%; Purity: 93%; LCMS: m/z 753.6 [M+H]$^+$ Synthesis of peptide (6) Palm-Ala-Ala-Pro-Ala-Lys-NH$_2$ (see SEQ ID NO:6)

The peptide was palmitoylated according to protocol P1 then the peptide was cleaved from the resin and was purified by preparative HPLC. Yield: 75%; Purity: 99%; LCMS: m/z 694.6 [M+H]$^+$ Synthesis of peptide (9) Palm-Arg-Pro-Ala-Lys-OH (see SEQ ID NO:9)

The peptide was palmitoylated according to protocol P1 then the peptide was cleaved from the resin and was purified by preparative HPLC. Yield: 60%; Purity: 99%; LCMS: m/z 709.6 [M+H]$^+$ The peptides whose use is the object of the invention were subjected to pharmacological tests for purposes of showing their anti-hair-loss and hair regrowth activity.

II. Evaluation of the Biological Activity of 9 Peptides

1) Study of the Effect of the Peptides on the Proliferation and on the Viability of Cells Forming Part of the Human Hair Follicle Cell proliferation and viability were evaluated in vitro with a kit from Promega, CellTiter-Blue® Cell Viability Assay, for estimating the number of living cells present in the culture. This kit is based on detection, by measurement of fluorescence, of conversion of the dye, resazurin, into a fluorescent product (resorufin) by living and thus metabolically active cells.

The effect of the peptides tested, (1) and (9), at 4 different concentrations ($10^{-5}$, $10^{-7}$, $10^{-9}$ and $10^{-11}$M) was examined on five cell types: immortalized human skin keratinocytes (HaCaT), human hair follicular keratinocytes (HHFK), normal human dermal fibroblasts (NHDF), hair follicle dermal papilla cells (HFDPC), and normal human epidermal melanocytes (NHEM) exposed to the molecule studied for 72 hours.

The results obtained show that all the peptides studied at the 4 concentrations tested have no toxicity with respect to the four cell types used in this experiment.

In addition, mild stimulation of proliferation of NHDF by (6) at $10^{-5}$M (+11%) and of HaCaT by (1) at $10^{-5}$M (+15%) was observed.

2) Quantitative PCR (TLDA) Analysis of Expression of Genes Encoding the Protein Factors Potentially Involved in Male Androgenetic Alopecia To study the effect of 9 peptides on these genes, HFDPC were treated for 24 hours with the molecules tested at $10^{-7}$M and $10^{-9}$M concentrations.

RNA was extracted and purified from cell pellets using the RNA XS Kit (Macherey-Nagel). RNA quantification was carried out with a NanoDrop device and sample quality was verified on a Bioanalyzer with RNA 6000 Nano chips (Agilent). cDNA was synthesized from 300 ng of RNA using the High-Capacity cDNA Reverse Transcription Kit (LifeTech). Quality-control qPCR assays of the cDNA were carried out in microplates on the reference gene, GAPDH, and the SIRT1 gene.

Final qPCR experiments were carried out in a 1 µl volume on microfluidic cards (TaqMan Low Density Arrays, LifeTech) and the ABI 7900HT qPCR device. Amplification reactions were performed in duplicate using 1 to 2 ng of cDNA per qPCR reaction and TaqMan Universal Master Mix II (LifeTech).

Ct values were obtained using the RQ Manager software. For analyses of qPCR results, Ct values were limited to 35 cycles and the duplicate assays are averaged. The GeneXPro software was used for the studies of stability and of selection of the best reference genes. Expression variations are calculated by the relative quantification method and are expressed as percent increase in expression of the gene of interest relative to the untreated controls.

The results, presented in Table 1, show that (1), (2), (3), (5), (6) and (9) stimulate several genes whose expression is reduced in subjects characterized by alopecia. The intensity of the effect varies as a function of the structure and of the concentration of the peptide tested.

TABLE 1 qPCR analysis of the in vitro effect of the peptides ($10^{-5}$ M) on modification of expression of genes encoding growth factors involved in hair growth

| | | | | % stimulation | | |
|---|---|---|---|---|---|---|
| Formulae | KGF | HGF | PDGF | VEGF | IGF1 | BMP2 |
| 1 H-Ala-Arg-Pro-Ala-Lys-OH | 14% | | | | 32% ($10^{-7}$) | 26% ($10^{-7}$) |
| 2 Palm-Ala-Arg-Pro-Ala-His-OH | 71% | | 29% | 11% | 136% ($10^{-9}$) | |
| 3 Palm-Ala-Arg-Pro-Ala-Lys-NH$_2$ | | | | 83% | | |
| 4 Palm-Ala-Arg-Pro-Ala-Ala-NH$_2$ | | | | | | |
| 5 Palm-Ala-Arg-Ala-Ala-Lys-NH$_2$ | | | | 10% | 29% ($10^{-7}$) | |
| | | | | | 16% ($10^{-9}$) | |
| 6 Palm-Ala-Ala-Pro-Ala-Lys-NH$_2$ | | | | 24% | 94% ($10^{-9}$) | 116% ($10^{-9}$) |
| 7 Chol-Ala-Arg-Pro-Ala-Lys-NH$_2$ | | 49% | | | | |
| 8 H-Arg-Pro-Lys-OH | 14% | | | | | |
| 9 Palm-Arg-Pro-Ala-Lys-OH | 156% | | 304% | 93% | | |

Study performed on HFDPC

3) Study of the Effect of the Peptides on Secretion of Growth Factors Involved in Regulation of the Hair Cycle Considering the fact that hair growth is controlled by numerous growth factors whose role is well established, the capacity of the peptides to induce hair cells to secrete these factors was evaluated. Furthermore, it would be interesting to know if these peptides have an effect on secretion of protein factors encoded by genes suppressed in alopecia and whose expression was increased following treatments with the compounds tested.

NHDF, HFDPC, HHFK and NHEM cells were treated with the peptides studied for 48h. At the end of the treatment, cell supernatants were collected and stored at −80° C. until analysis. The factors of interest secreted into the supernatant were assayed by ELISA® (R&D) or BioPlex® (BioRad®).

The results obtained (Table 2) demonstrated a stimulatory effect of the peptides at concentrations of $10^{-7}$M and $10^{-5}$M on secretion of several growth factors involved in hair growth, such as PDGF, KGF, VEGF, HGF, SCF, NGF. In addition, treatment of cells forming part of the hair follicle led to an increase in secretion of protein factors encoded by genes whose expression is reduced in subjects developing alopecia (BMP2). (6) as well as (1) show the most significant activity.

The results are expressed as percent increase in the concentration of the factor present in the supernatant relative to the untreated control. The intensity of the effect varies as a function of the concentration of the peptide studied and of the cell type treated.

TABLE 2

In vitro effect of the peptides on secretion by hair follicle cells of factors involved in hair growth

| Peptide | [M] | HFDPC | NHDF | HHFK | NHEM |
|---|---|---|---|---|---|
| (6) | $10^{-7}$ | PDGF 38% | NGF 12% | HGF 52% | VEGF 15% |
| | | KGF 13% | VGF 407% | SCF 9% | |
| | | | | NGF 10% | |
| | $10^{-5}$ | PDGF 15% | VEGF 40%, | NT | NT |
| | | KGF 7% | 275% | | |
| | | VEGF 18% | NGF 51% | | |
| | | BMP2 44% | SCF 8% | | |
| (1) | $10^{-7}$ | PDGF 31% | VEGF 4% | | |
| | | KGF 8% | | | |
| | | VEGF 9% | | | |
| | $10^{-9}$ | PDGF 23% | VEGF5% | | |
| | | KGF 25% | HGF 18% | | |
| | | VEGF 4% | NGF 13% | | |
| | | BMP2 22% | | | |
| (5) | $10^{-7}$ | PDGF 55% | HGF 21% | HGF 104% | VEGF 5% |
| | | | | | HGF 8% |
| | $10^{-5}$ | PDGF 39% | VEGF 12% | NT | NT |
| | | | NGF 15% | | |
| (3) | $10^{-7}$ | KGF 53% | NT | | |
| | | VEGF 9% | | | |
| | $10^{-9}$ | PDGF 39% | VEGF 48% | | |
| | | KGF 45% | HGF 5% | | |
| | | HGF 33% | NGF 89% | | |
| | | NGF 6% | | | |
| (7) | $10^{-7}$ | NT | HGF 104% | | |
| | | | SCF 10% | | |
| | | | NGF 11% | | |
| | $10^{-9}$ | NT | NT | | |
| (4) | $10^{-7}$ | PDGF 8% | HGF 188% | | |
| | | | VEGF 9% | | |
| | | | SCF 6% | | |
| | | | NGF 12% | | |
| | $10^{-9}$ | NT | HGF 95% | | |
| | | | SCF 8% | | |
| | | | NGF 18% | | |
| (9) | $10^{-7}$ | PDGF 117% | SCF 8% | HGF 94% | |
| | | | | SCF 11% | |
| | $10^{-5}$ | PDGF 62% | VEGF 24% | | |
| | | VEGF 10% | | | |
| (2) | $10^{-7}$ | HGF 565% | HGF 13% | HGF 28% | |
| | | | SCF 37% | | |
| | $10^{-5}$ | HGF 403% | SCF 24% | | |
| (8) | $10^{-7}$ | HGF 129% | | | |
| | $10^{-5}$ | HGF 26% | HGF 8% | | |

NT not tested

III. Study of the Stimulatory Activity of (1), (6) and (9) on the Growth of Isolated Hair ex vivo, and on Associated Morphological Changes This study was carried out on microdissected hairs from scalp surgery specimens from women aged 52 to 71 years. Isolated hairs were kept alive for 11 to 12 days in Williams medium, under conventional cell culture conditions (37° C., 5% $CO_2$). The peptide is added to the culture medium at two concentrations: $10^{-7}$M and $10^{-9}$M, every 2 days. minoxidil (2,4-diamino 6-piperidinopyrimidine 3-oxide) sulphate was used as positive control at a concentration of $10^{-5}$ M.

To evaluate the effect of (1), (6) or (9) on hair growth, the hairs were photographed and their lengths measured using image analysis software. Thus, the growth of the hairs between D0 and D11/D12 could be calculated and compared with that of the untreated control. At the end of the treatments (D11 or D12), the hairs were collected and frozen or fixed for immunolabeling and histological staining.

The results obtained, summarized in Table 3, show that peptides (1) and (6), and to a lesser extent (9), stimulate hair growth after 11 to 12 days of treatment ex vivo.

The growth increase with (1) at $10^{-9}M$ is close to that obtained after treatment with minoxidil sulphate (+48% at D11). The growth increase with (6) at $10^{-9}M$ is higher than that obtained after treatment with minoxidil sulphate (+28% at D12).

In addition, these three peptides stimulate expression of follicular markers involved in regulation of stem cells (CK15, CK19), in follicular growth (IGF1), and in anchoring of the hair to the extracellular matrix (collagen IV, laminin-5).

TABLE 3

Ex vivo effect of 9 peptides on hair growth

| Vs | (1) | | (6) | | (9) | |
|---|---|---|---|---|---|---|
| Control | $10^{-1}$ M | $10^{-9}$ M | $10^{-7}$ M | $10^{-9}$ M | $10^{-7}$ M | $10^{-9}$ M |
| Growth at D 11/D 12 | No effect | +40% | +28% | +38%# | No effect | +5% |
| Follicular markers | | ↗ IGF1 Laminin-5 Coll IV | ↗ CK19 CD34 Coll IV | | ↗ CK19 CK15 | ↗ CK19 CK15 |

↗ increase;
Student's t-test with p < 0.1.

This invention relates to hair growth stimulants containing as active ingredient synthetic peptides of the general formula $A$-$X_1$—$X_2$-Pro-Ala-$X$—$B$. As a whole, the observations obtained under the experimental conditions of this study identify these peptides as activators of the gene expression suppressed in alopecia as well as stimulators of production of the growth factors essential for hair growth.

Ex vivo evaluation of biological activity demonstrates their hair growth-inducing effect. The peptides studied induce the set of changes described at concentrations varying between $10^{-9}M$ and $10^{-5}M$. Thus, the preparation according to the invention can be effectively employed as preparation for external use, such as a pharmaceutical or cosmetic product for promoting hair growth and/or for increasing hair density and/or for reducing hair loss.

The following formulation examples further illustrate the present invention:

Example 1

Lotion Comprising Peptide (1)

| | In g |
|---|---|
| Peptide (1) | $5 \cdot 10^{-6}$ |
| 95° ethanol | 20 |
| Propylene glycol | 10 |
| Water, preservatives | qs 100 |

Example 2

Lotion Comprising Peptide (9)

| | In g |
|---|---|
| Peptide | $10^{-5}$ |
| Water | 81 |
| Keltrol T | 0.5 |
| Techpolymer MB −4° C. | 1 |
| Sepigel 305 | 0.5 |
| Silicone Oil 140 | 2 |
| Butylene Glycol | 5 |

The invention claimed is:

1. A peptide conjugate of formula Palm-Ala-Ala-Pro-Ala-Lys-NH$_2$ (SEQ ID NO:6) or a dermatologically acceptable salt thereof,
wherein
Palm represents a palmitoyl group.

2. The peptide conjugate according to claim 1, wherein said salt is an acid addition salt.

3. The peptide conjugate according to claim 2, wherein said acid is hydrochloric acid, trifluoroacetic acid, and/or acetic acid.

4. A topical dermatological composition comprising the peptide conjugate of claim 1 or a dermatologically acceptable salt thereof.

5. The composition according to claim 4, characterized in that it is a composition for the scalp.

6. The composition according to claim 4, wherein said composition is a lotion, a shampoo, a spray, a gel, or a cream.

7. The composition according to claim 6, wherein said shampoo is a medicated shampoo.

8. The composition according to claim 4, wherein the concentration of the peptide conjugate or a dermatologically acceptable salt thereof ranges between $10^{-9}$ and $10^{-4}$ mole/litre of the composition.

9. The composition according to claim 4, wherein said composition further comprises minoxidil, nicotinic acid esters, 5a-reductase inhibitors, and/or another peptide with dermatological activity.

10. The composition according to claim 4, wherein said composition further comprises minoxidil.

11. A method for treating alopecia in a person in need thereof, said method comprising administering to said person the peptide conjugate of claim 1 or a dermatologically acceptable salt thereof.

12. The method according to claim 8, wherein the alopecia is androgenetic, congenital, acquired, localized, diffuse, acute, or chronic alopecia.

13. The method according to claim 11, wherein said peptide conjugate or a dermatologically acceptable salt thereof is used in combination with another dermatological active ingredient.

14. The method according to claim 13, wherein said dermatological active ingredient is minoxidil, a nicotinic acid ester, a 5α-reductase inhibitor, another peptide with dermatological activity, or combinations thereof.

* * * * *